United States Patent
Nishiyama et al.

(10) Patent No.: US 11,446,635 B2
(45) Date of Patent: Sep. 20, 2022

(54) CATALYST AND METHOD FOR PRODUCING SAME, AND METHOD FOR PRODUCING DIENE COMPOUND USING SAID CATALYST

(71) Applicant: SEKISUI CHEMICAL CO., LTD., Osaka (JP)

(72) Inventors: Haruka Nishiyama, Ibaraki (JP); Noritoshi Yagihashi, Ibaraki (JP); Toshihito Miyama, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 11 days.

(21) Appl. No.: 16/763,653

(22) PCT Filed: Dec. 27, 2018

(86) PCT No.: PCT/JP2018/048182
§ 371 (c)(1),
(2) Date: May 13, 2020

(87) PCT Pub. No.: WO2019/131890
PCT Pub. Date: Jul. 4, 2019

(65) Prior Publication Data
US 2020/0276562 A1 Sep. 3, 2020

(30) Foreign Application Priority Data

Dec. 27, 2017 (JP) .............................. JP2017-252590

(51) Int. Cl.
*B01J 23/30* (2006.01)
*B01J 23/06* (2006.01)
(Continued)

(52) U.S. Cl.
CPC .............. *B01J 23/30* (2013.01); *B01J 21/066* (2013.01); *B01J 23/06* (2013.01); *B01J 23/20* (2013.01);
(Continued)

(58) Field of Classification Search
CPC .......... B01J 23/30; B01J 21/066; B01J 23/06; B01J 23/20; B01J 23/22; B01J 35/1061;
(Continued)

(56) References Cited

U.S. PATENT DOCUMENTS 2,421,361 A * 5/1947 Toussaint .............. C07C 1/2072
585/606
4,560,822 A * 12/1985 Hoelderich ............... C07C 1/24
585/606
(Continued)

FOREIGN PATENT DOCUMENTS

| CN | 104437616 | 3/2015 |
|---|---|---|
| CN | 106861752 | 6/2017 |

(Continued)

OTHER PUBLICATIONS

Trees De Baerdemaeker et al., "Bimetallic Zn and Hf on Silica Catalysts for the Conversion of Ethanol to 1,3-Butadiene", ACS Catalysis, 2015, vol. 5, No. 6, pp. 3393-3397.
(Continued)

*Primary Examiner* — Patricia L. Hailey
(74) *Attorney, Agent, or Firm* — Wenderoth, Lind & Ponack, L.L.P.

(57) ABSTRACT

The present invention relates to a catalyst which is a composite oxide including at least one element X selected from the group consisting of elements belonging to Groups 3 to 6 of the periodic table, and at least one element Z
(Continued)

selected from the group consisting of elements belonging to Group 14 of the periodic table, wherein the catalyst has mesopores.

14 Claims, 1 Drawing Sheet

(51) Int. Cl.
  *B01J 23/20* (2006.01)
  *B01J 23/22* (2006.01)
  *B01J 35/10* (2006.01)
  *B01J 37/03* (2006.01)
  *B01J 37/08* (2006.01)
  *C07C 1/20* (2006.01)
  *B01J 21/06* (2006.01)

(52) U.S. Cl.
  CPC .......... *B01J 23/22* (2013.01); *B01J 35/1061* (2013.01); *B01J 37/03* (2013.01); *B01J 37/088* (2013.01); *C07C 1/20* (2013.01); *C07C 2521/06* (2013.01); *C07C 2521/08* (2013.01); *C07C 2523/06* (2013.01); *C07C 2523/20* (2013.01); *C07C 2523/22* (2013.01); *C07C 2523/30* (2013.01)

(58) Field of Classification Search
  CPC .......... B01J 37/03; B01J 37/088; C07C 1/20; C07C 2521/06; C07C 2521/08; C07C 2523/06; C07C 2523/20; C07C 2523/22; C07C 2523/30
  USPC ................ 502/242, 246–248, 254, 524, 525; 585/607, 609
  See application file for complete search history.

(56) References Cited

U.S. PATENT DOCUMENTS

| | | | |
|---|---|---|---|
| 6,491,886 | B1 | 12/2002 | Hedouin et al. |
| 9,878,965 | B2* | 1/2018 | Spannhoff ............ B01J 37/0045 |
| 2014/0179973 | A1 | 6/2014 | Debecker et al. |
| 2015/0151292 | A1 | 6/2015 | Suh et al. |
| 2017/0260112 | A1 | 9/2017 | Nishino et al. |
| 2018/0200694 | A1* | 7/2018 | Cadran ................ B01J 37/0201 |
| 2018/0200696 | A1* | 7/2018 | Cadran ................ B01J 35/1061 |
| 2018/0208522 | A1 | 7/2018 | Cadran et al. |
| 2021/0170364 | A1* | 6/2021 | Nishiyama ........... B01J 35/1061 |

FOREIGN PATENT DOCUMENTS

| | | |
|---|---|---|
| JP | 2000-511111 | 8/2000 |
| JP | 2000-288347 | 10/2000 |
| JP | 2015-168644 | 9/2015 |
| JP | 2015-527192 | 9/2015 |
| JP | 2016-518395 | 6/2016 |
| WO | 2014/061917 | 4/2014 |
| WO | 2014/129248 | 8/2014 |
| WO | 2014/180778 | 11/2014 |
| WO | 2014/199349 | 12/2014 |
| WO | 2016/043209 | 3/2016 |
| WO | 2017/009107 | 1/2017 |

OTHER PUBLICATIONS

Matthew D. Jones et al., "Investigations into the conversion of ethanol into 1,3-butadiene", Catalysis Science & Technology, 2011, vol. 1, No. 2, pp. 267-272.
Extended European Search Report dated Aug. 12, 2021 in European Patent Application No. 18897012.3.
International Search Report dated Mar. 19, 2019 in International (PCT) Application No. PCT/JP2018/048182.

* cited by examiner

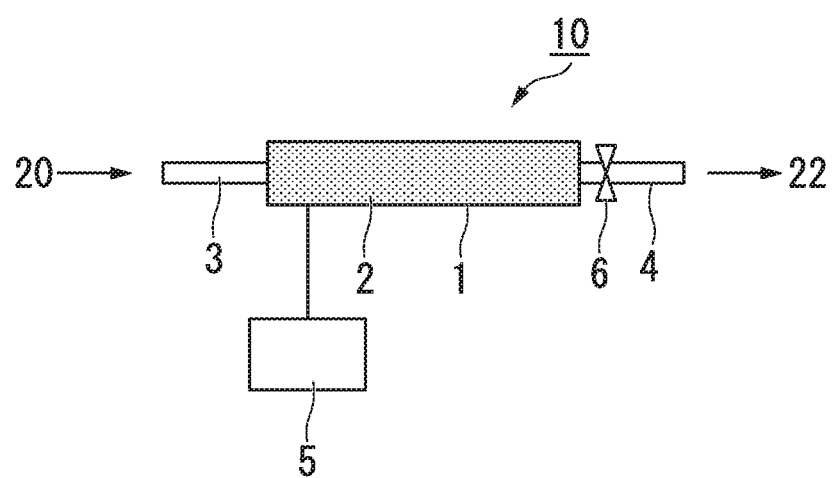

CATALYST AND METHOD FOR PRODUCING SAME, AND METHOD FOR PRODUCING DIENE COMPOUND USING SAID CATALYST

TECHNICAL FIELD

The present invention relates to a catalyst, a method for producing the same, and a method for producing a diene compound using the catalyst.

Priority is claimed on Japanese Patent Application No. 2017-252590, filed on Dec. 27, 2017, the content of which is incorporated herein by reference.

BACKGROUND ART

Butadiene such as 1,3-butadiene, which is a representative example of diene compounds, is used as a raw material for styrene-butadiene rubber (SBR) and the like. Conventionally, butadiene has been purified from the C4 fraction. The C4 fraction is a fraction obtained as a by-product in naphtha cracking for producing ethylene from petroleum. However, the use of petroleum has decreased as a result of increased use of shale gas. Consequently, the butadiene production by naphtha cracking of petroleum has also decreased. Therefore, there is a demand for an alternative method for producing diene compounds such as 1,3-butadiene.

For example, Patent Document 1 discloses an invention relating to a metal-impregnated silica catalyst for selectively converting ethanol into butadiene. More specifically, Patent Document 1 describes a butadiene synthesis catalyst including Hf and two or more catalytically active metals M1 and M2, wherein the two or more catalytically active metals M1 and M2 are selected from the group consisting of Zr, Zn, Cu, and combinations thereof, provided that M1 and M2 are different.

Patent Document 1 describes a method for synthesizing butadiene, which includes (i) providing a gas stream G-1 containing ethanol and optional acetaldehyde, and (ii) contacting the gas stream G-1 with the butadiene synthesis catalyst to obtain a gas stream G-2 containing butadiene.

Patent Document 1 describes that the method for synthesizing butadiene achieves a butadiene selectivity of at least 10%.

DESCRIPTION OF PRIOR ART

Patent Document

Patent Document 1: International Patent Application Publication No. 2014/199349

DISCLOSURE OF INVENTION

Problems to be Solved by the Invention

Although the invention described in Patent Document 1 enables butadiene synthesis using ethanol as a raw material gas, it is necessary to reduce the ethanol concentration in the raw material gas. For this reason, according to the invention described in Patent Document 1, the yield of butadiene per unit time is low, and it is difficult to increase the production efficiency of butadiene.

In this situation, the object of the present invention is to provide a catalyst that can efficiently produce a diene compound even when the alcohol concentration in the raw material gas is high.

Means to Solve the Problems

The present inventors have made intensively studies to solve the above-mentioned problems. As a result, they have found that the above problems can be solved by a specific catalyst having mesopores, and have completed the present invention.

That is, the embodiments of the present invention are as follows.

[1] A catalyst which is a composite oxide including at least one element X selected from the group consisting of elements belonging to Groups 3 to 6 of the periodic table, and at least one element Z selected from the group consisting of elements belonging to Group 14 of the periodic table, wherein the catalyst has mesopores.

[2] The catalyst according to [1], which satisfies formula 1:

$$X_{a1}Si_{b1}O_{\delta 1} \qquad \text{Formula 1}$$

wherein:

a1 is a molar ratio of the element X, and is 0.1 to 20 mol % with the proviso that a sum of a1 and b1 is 100 mol %;

b1 is a molar ratio of Si, and is 80 to 99.9 mol % with the proviso that a sum of a1 and b1 is 100 mol %; and δ1 represents a number required to satisfy a charge neutral condition.

[3] The catalyst according to claim [1] or [2], which further includes a zinc element (Zn).

[4] The catalyst according to [3], which satisfies formula 2:

$$X_{a2}Si_{b2}Zn_{c2}O_{\delta 2} \qquad \text{Formula 2}$$

wherein:

a2 is a molar ratio of the element X, and is 0.1 to 20 mol % with the proviso that a sum of a2, b2 and c2 is 100 mol %;

b2 is a molar ratio of Si, and is 60 to 99.8 mol % with the proviso that a sum of a2, b2 and c2 is 100 mol %;

c2 is a molar ratio of Zn, and is 0.1 to 20 mol % with the proviso that a sum of a2, b2 and c2 is 100 mol %; and δ2 represents a number required to satisfy a charge neutral condition.

[5] The catalyst according to any one of [1] to [4], which is a catalyst for synthesizing a diene compound from a raw material gas containing an alcohol.

[6] The catalyst according to [5], wherein the raw material gas includes ethanol, acetaldehyde or a mixture of ethanol and acetaldehyde.

[7] A method for producing a catalyst, including:

a step of obtaining a solid colloid by preparing a mixture containing a compound containing at least one element X selected from the group consisting of elements belonging to Groups 3 to 6 of the periodic table, a compound containing at least one element Z selected from the group consisting of elements belonging to Group 14 of the periodic table, a surfactant, and a solvent containing water, and distilling off at least part of the solvent; and a step of calcining the solid colloid.

[8] The method according to [7], wherein the mixture further includes a compound containing zinc.

[9] A method for producing a diene compound, including contacting the catalyst of any one of [1] to [6] with a raw material gas containing an alcohol to produce a diene compound.

Effect of the Invention

The catalyst of the present invention enables efficient production of a diene compound even when the alcohol concentration in the raw material gas is high.

BRIEF DESCRIPTION OF THE DRAWINGS

FIG. 1 is a schematic view of an apparatus for producing butadiene according to one embodiment of the present invention.

DESCRIPTION OF THE EMBODIMENTS

Hereinbelow, embodiments of the present invention are described in detail, but the following descriptions illustrate only examples of the embodiments of the present invention, and the present invention is not limited thereto and may be modified as long as the modifications do not deviate from the gist of the present invention.

<Catalyst>

The catalyst is a composite oxide including at least one element X selected from the group consisting of elements belonging to Groups 3 to 6 of the periodic table, and at least one element Z selected from the group consisting of elements belonging to Group 14 of the periodic table, wherein the catalyst has mesopores. In the context of the present specification, the term "composite oxide" means an oxide containing two or more elements other than oxygen.

The presence of the element X enables the raw material gas to be converted into a diene compound. Further, the contact area between the raw material gas and the catalyst can be increased by the presence of the element Z. Furthermore, the catalyst, being a composite oxide, can produce a diene compound while suppressing the formation of byproducts.

Examples of the element X include Group 3 elements such as scandium (Sc), yttrium (Y), lanthanum (La), and cerium (Ce); Group 4 elements such as titanium (Ti), zirconium (Zr), and hafnium (Hf); Group 5 elements such as vanadium (V), niobium (Nb), and tantalum (Ta); and Group 6 elements such as chromium (Cr), molybdenum (Mo), and tungsten (W). Of these, Group 3 elements, Group 4 elements and Group 5 elements are preferable, Group 4 elements and Group 5 elements are more preferable, and Group 4 elements are even more preferable.

According to another embodiment, the element X is preferably a Group 5 element, a Group 6 element, or a Group 7 element, and more preferably a Group 5 element, or a Group 6 element. Specifically, yttrium (Y), lanthanum (La), cerium (Ce), titanium (Ti), zirconium (Zr), hafnium (Hf), vanadium (V), niobium (Nb), tantalum (Ta), molybdenum (Mo) and tungsten (W) are preferable; yttrium (Y), lanthanum (La), cerium (Ce), titanium (Ti), zirconium (Zr), hafnium (Hf), niobium (Nb) and tantalum (Ta) are more preferable; zirconium (Zr), hafnium (Hf), niobium (Nb) and tantalum (Ta) are even more preferable; zirconium (Zr), hafnium (Hf) and niobium (Nb) are even more preferable; zirconium (Zr) and hafnium (Hf) are particularly preferable; and hafnium (Hf) is most preferable.

One of the elements X described above may be used alone, or two or more thereof may be used in combination.

The molar amount of the element X is preferably 0.1 to 20 mol %, more preferably 1 to 15 mol %, even more preferably 1 to 6 mol %, and particularly preferably 1.75 to 3 mol %, with the proviso that the sum of the molar ratio of the element X and the molar ratio of the element Z in the catalyst is 100 mol %. When two or more different elements X are used in combination, the sum of the amounts thereof is preferably within in the above range.

Examples of the element Z include carbon (C), silicon (Si), germanium (Ge), and tin (Sn).

Among these, the element Z is preferably carbon (C) or silicon (Si), and more preferably silicon (Si).

One of the elements Z described above may be used alone, or two or more thereof may be used in combination.

The molar amount of the element Z may be 80 to 99.9 mol %, more preferably 85 to 99 mol %, and even more preferably 94 to 99 mol %, with the proviso that the sum of the molar ratio of the element X and the molar ratio of the element Z in the catalyst is 100 mol %. When two or more different elements Z are used in combination, the sum of the amounts thereof is preferably within in the above range.

In one preferred embodiment, the catalyst preferably satisfies the following formula 1:

$$X_{a1}Si_{b1}O_{\delta1} \qquad \text{Formula 1}$$

In the formula 1, X represents the element X.

In the formula 1, a1 is a molar ratio of the element X, and is 0.1 to 20 mol %, preferably 1 to 15 mol %, more preferably 1 to 6 mol %, and even more preferably 1.75 to 3 mol %, with the proviso that the sum of a1 and b1 is 100 mol %.

In the formula 1, b1 is a molar ratio of Si, and is 80 to 99.9 mol %, preferably 85 to 99 mol %, and more preferably 94 to 99 mol %, with the proviso that the sum of a1 and b1 is 100 mol %.

In the formula 1, $\delta1$ represents a number required to satisfy a charge neutral condition. Specifically, $\delta1$ depends on the elements X and Si constituting the catalyst, as well as a1 and b1. In one embodiment, $\delta1$ is preferably from 100 to 2000, more preferably from 100 to 1000, and even more preferably from 100 to 400.

As long as the effect of the present invention is not impaired, the catalyst of the present embodiment may include an element other than the element X and the element Z as a constituent element of the composite oxide.

In one embodiment, the catalyst preferably further include a zinc element (Zn). The presence of the zinc element (Zn) in the catalyst is favorable in that the selectivity for the diene compound, the raw material conversion, and the yield of the diene compound are improved.

That is, the present invention in one preferred embodiment thereof provides a catalyst which is a composite oxide including at least one element X selected from the group consisting of elements belonging to Groups 3 to 6 of the periodic table, at least one element Z selected from the group consisting of elements belonging to Group 14 of the periodic table, and a zinc element (Zn), wherein the catalyst has mesopores.

The molar amount of the element X in the case where the catalyst contains a zinc element is preferably 0.1 to 20 mol %, more preferably 1 to 15 mol %, even more preferably 1 to 6 mol %, and particularly preferably 1.75 to 3 mol %, with the proviso that the sum of the molar ratio of the element X, the molar ratio of the element Z and the molar ratio of zinc in the catalyst is 100 mol %. When two or more different elements X are used in combination, the sum of the amounts thereof is preferably within in the above range.

The molar amount of the element Z in the case where the catalyst contains a zinc element is preferably 60 to 99.8 mol %, more preferably 70 to 98 mol %, and even more preferably 88 to 98 mol %, with the proviso that the sum of the molar ratio of the element X, the molar ratio of the element Z and the molar ratio of zinc in the catalyst is 100 mol %. When two or more different elements Z are used in combination, the sum of the amounts thereof is preferably within in the above range.

The molar ratio of the zinc element (Zn) is preferably 0.1 to 20 mol %, more preferably 0.1 to 10 mol %, even more preferably 0.1 to 7.5 mol %, particularly preferably 1.2 to 5 mol %, and most preferably 1.5 to 3 mol %, with the proviso that the sum of the molar ratio of the element X, the molar ratio of the element Z and the molar ratio of zinc in the catalyst is 100 mol %.

When an element other than the element X and the element Z (hereinafter, also referred to as "other element") is included as a constituent element of the composite oxide, the balance of the molar ratios of the element X, the element Z, and other element are preferably such that, as mentioned above, the molar ratio of the element Z is reduced in an amount corresponding to the molar ratio of the other element. In other words, the molar ratio of the element X preferably stays the same regardless of whether the other element is included or not. The same applies to the case where two or more other elements are included.

In one preferred embodiment, the catalyst preferably satisfies the following formula 2:

$$X_{a2}Si_{b2}Zn_{c2}O_{\delta2} \qquad \text{Formula 2}$$

In the formula 2, X represents the element X.

In the formula 2, a2 is a molar ratio of the element X, and is 0.1 to 20 mol %, preferably 1 to 15 mol %, more preferably 1 to 6 mol %, and even more preferably 1.75 to 3 mol %, with the proviso that a sum of a2, b2 and c2 is 100 mol %.

In the formula 2, b2 is a molar ratio of Si, and is preferably 60 to 99.8 mol %, more preferably 70 to 98 mol %, and even more preferably 88 to 98 mol %, with the proviso that the sum of a2, b2 and c2 is 100 mol %.

In the formula 2, c2 is a molar ratio of the element Zn, and is 0.1 to 20 mol %, preferably 0.01 to 10 mol %, more preferably 0.1 to 7.5 mol %, even more preferably 1.2 to 5 mol %, and particularly preferably 1.5 to 3 mol %, with the proviso that the sum of a2, b2 and c2 is 100 mol %.

In the formula 2, $\delta2$ represents a number required to satisfy a charge neutral condition. Specifically, $\delta2$ depends on the elements X and Si constituting the catalyst, as well as a2, b2 and c2. In one embodiment, $\delta2$ is preferably from 100 to 2000, more preferably from 100 to 1000, and even more preferably from 100 to 400.

The catalyst of the present embodiment has mesopores. The presence of mesopores in the catalyst improves the diffusion of alcohol into the catalyst and increases the contact area between the alcohol and the catalyst. As a result, even when the alcohol concentration is high, the raw material conversion and the diene compound selectivity are improved. In the context of the present specification, the catalyst having mesopores means that the catalyst is porous with an average pore diameter of 2 to 50 nm, preferably 2 to 30 nm, and more preferably 2 to 15 nm. The "average pore diameter" of the catalyst is a value measured by the following method. That is, the average pore diameter is calculated from the total pore volume (total of the pore volumes of the catalyst) and the BET specific surface area. Specifically, the average pore diameter can be calculated on the assumption that the pores are in the form of a cylinder (BJH method). With the BET specific surface area A1 being used as the side area of the cylinder and the total pore volume V1 being used as the volume of the cylinder, the average pore diameter can be calculated by 4V1/A1.

The total pore volume of the catalyst is preferably 0.1 to 10.0 mL/g, more preferably 0.1 to 5.0 mL/g, and even more preferably 0.1 to 2.0 mL/g. The total pore volume of not less than 0.1 mL/g is favorable in that the diffusibility of the alcohol is improved, and the raw material conversion and the diene compound selectivity are further increased. On the other hand, the total pore volume of not more than 10.0 mL/g is favorable in that the contact area between the alcohol and the catalyst increases, so that the raw material conversion and the butadiene selectivity are further increased. In the context of the present specification, the "total pore volume" of the catalyst is a value measured by a gas adsorption method. The gas adsorption method is a method in which nitrogen gas is used as an adsorption gas, nitrogen molecules are allowed to be adsorbed on the surface of the synthesis catalyst, and pore distribution is measured from condensation of the molecules.

The specific surface area of the catalyst is preferably 100 to 10000 m²/g, more preferably 200 to 5000 m²/g, and even more preferably 200 to 1000 m²/g. The specific surface area of not less than 100 m²/g is favorable in that a sufficient amount of active sites are provided on the catalyst surface, which allows for further increase in the raw material conversion and the diene compound selectivity. As a result, the raw material conversion is increased even when the raw material concentration is high with respect to 100% by volume of the raw material gas (in terms of gas volume). For example, a high raw material conversion is achieved even with the raw material concentration of 100% by volume. On the other hand, the specific surface area of not more than 10000 m²/g is favorable in that the contact area between the alcohol and the catalyst increases, and the raw material conversion and the diene compound selectivity are further increased. In the context of the present specification, the specific surface area means the BET specific surface area, which is measured by the BET gas adsorption method using nitrogen as an adsorption gas.

The product of the total pore volume times the specific surface area of the catalyst is preferably 10 to 100000 mL·m²/g², more preferably 20 to 25000 mL·m²/g², and even more preferably 20 to 2000 mL·m²/g². The product of not less than 10 mL·m²/g² is favorable in that a sufficient amount of active sites are provided on the catalyst surface and the diffusivity of the raw material gas containing an alcohol is improved, thereby allowing for further increase in the raw material conversion and the diene compound selectivity. On the other hand, the product of not more than 100000 mL·m²/g² is favorable in that the contact area between the raw material and the catalyst tends to be sufficient, and the raw material conversion and the diene compound selectivity are further increased.

The mesopore volume ratio (total mesopore volume/total pore volume×100) of the catalyst is preferably 50% or more, more preferably 50 to 100%, even more preferably 80 to 100%, and particularly preferably 90 to 100%. The mesopore volume ratio of 50% or more is favorable in that a sufficient amount of mesopores are provided in the catalyst and the diffusivity of the raw material gas containing an alcohol is improved, thereby allowing for further increase in the raw material conversion and the diene compound selectivity.

The ratio of the mesopore volume ratio can be controlled by changing the ratio of raw materials (the compound containing the element X, the compound containing the element Z, etc.) used in the production method described below, the calcination temperature in the calcination step, etc.

The shape of the mesopores and whether or not the pore walls forming the mesopores have a crystal structure can be determined by observing a diffraction peak obtained by X-ray diffractometry. Specifically, when the pore walls forming the mesopores of the synthesis catalyst have a crystal structure, a peak ascribed to the periodic structure of the mesopores is observed at a low angle of 2θ=1 to 6° in the X-ray diffraction pattern. The shape and regularity of the mesopores can be determined by observing the synthesis catalyst with a transmission electron microscope (TEM).

The catalyst described above is preferably a catalyst for synthesizing a diene compound from a raw material gas containing an alcohol. The alcohol is preferably ethanol as described later. In one preferred embodiment, the raw material gas includes ethanol and/or acetaldehyde. Further, the diene compound described above is preferably 1,3-butadiene as described below.

<Method for Producing Catalyst>

The present invention in another aspect provides a method for producing the catalyst. The method includes: a step of obtaining a solid colloid by preparing a mixture containing a compound containing at least one element X selected from the group consisting of elements belonging to Groups 3 to 6 of the periodic table, a compound containing at least one element Z selected from the group consisting of elements belonging to Group 14 of the periodic table, a surfactant, and a solvent containing water, and distilling off at least part of the solvent (solid colloid preparation step); and a step of calcining the solid colloid (calcination step).

[Solid Colloid Preparation Step]

The solid colloid preparation step is a step of obtaining a solid colloid by preparing a mixture containing a compound containing at least one element X selected from the group consisting of elements belonging to Groups 3 to 6 of the periodic table, a compound containing at least one element Z selected from the group consisting of elements belonging to Group 14 of the periodic table, a surfactant, and a solvent containing water, and distilling off at least part of the solvent.

(Mixture)

The mixture contains: a compound containing at least one element X selected from the group consisting of elements belonging to Groups 3 to 6 of the periodic table; a compound containing at least one element Z selected from the group consisting of elements belonging to Group 14 of the periodic table; a surfactant; and a solvent containing water. The mixture may further include a compound containing other element than mentioned above (e.g., a compound containing zinc), an acidic aqueous solution, a basic aqueous solution, and the like.

Compound Containing Element X

The compound containing the element X is not particularly limited. Examples thereof include inorganic salts such as chlorides, sulfides, nitrates, and carbonates; organic salts such as oxalate, acetylacetonate, dimethylglyoxime salt, and ethylenediamine acetate; chelate compounds; carbonyl compounds; cyclopentadienyl compounds; ammine complexes; alkoxide compounds; alkyl compounds; and the like.

Specific examples include titanium chloride ($TiCl_2$, $TiCl_3$, $TiCl_4$), zirconium chloride ($ZrCl_2$), hafnium chloride ($HfCl_4$), niobium chloride ($NbCl_5$), tantalum chloride ($TaCl_5$), vanadium chloride ($VCl_3$), tungsten chloride ($WCl_5$), scandium nitrate ($Sc(NO_3)_3$), yttrium nitrate ($Y(NO_3)_3$), lanthanum nitrate ($La(NO_3)_3$), and cerium nitrate ($Ce(NO_3)_3$).

One of the compounds containing the element X described above may be used alone, or two or more thereof may be used in combination.

The amount of the compound containing the element X to be used in the case where the catalyst does not contain the other element such as the zinc element is preferably 0.1 to 20 mol %, more preferably 1 to 15 mol %, even more preferably 1 to 6 mol %, and particularly preferably 1.75 to 3 mol %, with the proviso that the sum of the molar ratio of the compound containing the element X and the molar ratio of the compound containing the element Z is 100 mol %. When two or more different compounds containing elements X are used in combination, the sum of the amounts thereof is preferably within in the above range.

The amount of the compound containing the element X to be used in the case where the catalyst contains the other element such as the zinc element is preferably 0.1 to 20 mol %, more preferably 1 to 15 mol %, even more preferably 1 to 6 mol %, and particularly preferably 1.75 to 3 mol %, with the proviso that the sum of the molar ratio of the compound containing the element X, the molar ratio of the compound containing the element Z and the molar ratio of the compound containing the other element is 100 mol %. When two or more different compounds containing elements X are used in combination, the sum of the amounts thereof is preferably within in the above range.

Compound Containing Element Z

The compound containing the element Z is not particularly limited. Examples thereof include inorganic salts such as chlorides, sulfides, nitrates, and carbonates; organic salts such as oxalate, acetylacetonate, dimethylglyoxime salt, and ethylenediamine acetate; chelate compounds; carbonyl compounds; cyclopentadienyl compounds; ammine complexes; alkoxide compounds; alkyl compounds; and the like.

Among these, it is preferable to use an alkoxide compound containing silicon.

The alkoxide compound containing silicon is preferably a compound represented by the following formula 3:

$$Si(OR)_4 \qquad \text{Formula 3}$$

wherein each R independently represents an alkyl group. The alkyl group is preferably an alkyl group having 1 to 4 carbon atoms, and more preferably an ethyl group.

Specific examples of the alkoxide compound containing silicon include tetramethoxysilane, tetraethoxysilane, tetrapropoxysilane and the like. Of these, it is preferable to use tetraethoxysilane.

One of the compounds containing the element Z described above may be used alone, or two or more thereof may be used in combination.

The amount of the compound containing the element Z to be used in the case where the catalyst does not contain the other element such as the zinc element is preferably 80 to 99.9 mol %, more preferably 85 to 99 mol %, and even more preferably 94 to 99 mol %, with the proviso that the sum of the molar ratio of the compound containing the element X and the molar ratio of the compound containing the element Z is 100 mol %. When two or more different compounds containing elements Z are used in combination, the sum of the amounts thereof is preferably within in the above range.

The amount of the compound containing the element Z to be used in the case where the catalyst contains the other element such as the zinc element is preferably 60 to 99.8 mol %, more preferably 70 to 98 mol %, and even more preferably 88 to 98 mol %, with the proviso that the sum of the molar ratio of the compound containing the element X, the molar ratio of the compound containing the element Z and the molar ratio of the compound containing the other element is 100 mol %. When two or more different elements Z are used in combination, the sum of the amounts thereof is preferably within in the above range.

Compound Containing Zinc

The compound containing zinc is not particularly limited. Examples thereof include inorganic salts such as chlorides, sulfides, nitrates, and carbonates; organic salts such as oxalate, acetylacetonate, dimethylglyoxime salt, and ethylenediamine acetate; chelate compounds; carbonyl compounds; cyclopentadienyl compounds; ammine complexes; alkoxide compounds; alkyl compounds; and the like.

Specific examples include zinc chloride ($ZnCl_2$), zinc sulfide ($ZnS$), and zinc nitrate ($Zn(NO_3)_2$).

One of the compounds containing zinc described above may be used alone, or two or more thereof may be used in combination.

The amount of the compound containing zinc to be used is preferably 0.1 to 20 mol %, more preferably 0.1 to 10 mol %, even more preferably 0.1 to 7.5 mol %, particularly preferably 1.2 to 5 mol %, and most preferably 1.5 to 3 mol %, with the proviso that the sum of the molar ratio of the compound containing the element X, the molar ratio of the compound containing the element Z and the molar ratio of the compound containing zinc is 100 mol %.

Surfactant

By the use of the surfactant in the production of the catalyst, a catalyst with mesopores can be obtained. More specifically, the addition of the surfactant produces micelles which serve as template to form a precursor on the surfaces thereof. By subjecting the precursor to a calcination as described below, the surfactant is removed and a catalyst having mesopores can be produced. The shape of the micelles may be spherical, cylindrical, lamellar, gyroidal, or vesicle-like depending on the concentration of the surfactant.

The surfactant is not particularly limited and may be a cationic surfactant, a nonionic surfactant, etc.

Examples of the cationic surfactant include those conventionally used in the production of mesoporous silica, such as MCM-41, SBA-15, and FMS-16.

Examples of the nonionic surfactant include, but are not particularly limited to, a polyalkylene oxide block copolymer containing an alkylene oxide chain, and a compound in which the ends of the block copolymer is etherified with an alcohol, phenol, or the like.

Further, the alkylene oxide chains included as structural units may be of one type or of two or more types.

Of these, from the viewpoint of the stability of the crystal structure of the pore walls forming the mesopores of the obtained composite oxide, it is preferable to use a nonionic surfactant and more preferable to use a polyalkylene oxide block copolymer. From the viewpoint of the stability of the crystal structure of the pore walls forming the mesopores of the obtained composite oxide, it is even more preferable to use a polyalkylene oxide block copolymer having a polyethylene oxide chain $(CH_2CH_2O)_m$ and a polypropylene oxide chain $(CH_2CH(CH_3)O)_n$ as structural units, wherein m and n are 1 to 1000, preferably m is 1 to 200 and n is 1 to 100, more preferably m is 1 to 200 and n is 1 to 100, with the proviso that m+n is 2 to 300. The ends of the polymer may be a hydrogen atom, a hydroxyl group, or etherified with an alcohol or phenol.

From the viewpoint of the stability of the crystal structure of the pore walls forming the mesopores of the obtained compound oxide, it is especially preferable that the aforementioned polyalkylene oxide block copolymer is one presented by the formula 4:

$$HO(CH_2CH_2O)_r(CH_2CH(CH_3)O)_s(CH_2CH_2O)_tH \quad \text{Formula 4}$$

For obtaining the synthesis catalyst of the present invention with an average pore diameter within the preferable range described above, r is preferably 1 to 100, s is preferably 1 to 100, and t is preferably 1 to 100. Further, it is preferable that r+s+t is from 3 to 300.

The method for obtaining the polyalkylene oxide block copolymer is not particularly limited, and those synthesized by a conventionally known production method may be used, or commercially available products may be used.

Examples of the commercially available product of the polyalkylene oxide block copolymer include one with a product name P123 [$(HO(CH_2CH_2O)_{20}(CH_2CH(CH_3)O)_{70}(CH_2CH_2O)_{20})H$], one with a product name P85 [$(HO(CH_2CH_2O)_{26}(CH_2CH(CH_3)O)_{39}(CH_2CH_2O)_{26})H$], and one with a product name P103 [$(HO(CH_2CH_2O)_{56}(CH_2CH(CH_3)O)_{17}(CH_2CH_2O)_{56}H)$], each manufactured by BASF Co., Ltd.

One of the surfactants described above may be used alone, or two or more thereof may be used in combination.

The shape and diameter of the mesopores can be controlled by appropriately changing the type of the surfactant described above and the like.

The amount of the surfactant to be used is preferably 3 to 20 parts by mass, more preferably 5 to 18 parts by mass, and even more preferably 7 to 15 parts by mass, with respect to 100 parts by mass of the solvent. The use of the surfactant in an amount of 3 parts by mass or more is preferable in that the mesopores can be uniformly formed. On the other hand, the use of the surfactant in an amount of 20 parts by mass or less is preferable in that the surfactant can be dissolved.

Solvent

The solvent contains water. The solvent may further contain an organic solvent.

The water is not particularly limited, but is preferably ion-exchanged water or distilled water from which metal ions and the like have been removed.

Examples of the organic solvent include, but are not particularly limited to, aliphatic linear alcohols such as methanol, ethanol, n-propanol and n-hexanol.

Among these, the organic solvent is preferably methanol or ethanol from the viewpoint of handling.

One of the above organic solvents may be used alone, or two or more thereof may be used in combination.

The amount of water to be used is preferably 5 to 35 parts by mass, and more preferably 5 to 20 parts by mass, per 1 part by mass of the surfactant. The use of water in an amount of 5 parts by mass or more is preferable in that the surfactant can be dissolved. On the other hand, the use of water in an amount of 35 parts by mass or less is preferable in that the mesopores can be uniformly formed.

The amount of water to be used in the case where the catalyst does not contain the other element such as the zinc element is preferably 100 to 10000 mol %, and more preferably 1000 to 8000 mol %, with the proviso that the sum of the molar ratio of the compound containing the element X and the molar ratio of the compound containing the element Z is 100 mol %. The use of water in an amount of 100 mol % or more is favorable in that hydrolysis can be performed. On the other hand, the use of water in an amount of not more than 10000 mol % is favorable in that the solids are not dissolved.

The amount of water to be used in the case where the catalyst contains the other element such as the zinc element is preferably 100 to 10000 mol %, and more preferably 1000 to 8000 mol %, with the proviso that the sum of the molar ratio of the compound containing the element X, the molar ratio of the compound containing the element Z and the molar ratio of the compound containing the other element is 100 mol %. The use of water in an amount of 100 mol % or more is favorable in that hydrolysis can be performed. On the other hand, the use of water in an amount of not more than 10000 mol % is favorable in that the solids are not dissolved.

When an organic solvent is contained as the solvent, the amount of the organic solvent to be used is preferably from 10 to 50% by volume, and more preferably from 10 to 25% by volume, based on the volume of water. The use of the organic solvent in an amount of not less than 10% by volume is favorable in that the element X and the element Z can be dissolved. On the other hand, the use of the organic solvent in an amount of not more than 50% by volume is favorable in that hydrolysis can be performed.

Acidic Aqueous Solution

The acidic solution has a function of accelerating the generation of solids through the hydrolysis described below.

The acidic solution is not particularly limited, and examples thereof include an aqueous solution in which an inorganic acid such as hydrogen chloride, sulfuric acid, nitric acid, or phosphoric acid is dissolved.

The amount of the acidic solution to be used in the case where the catalyst does not contain the other element such as the zinc element is preferably 0.01 to 10.0 mol %, and more preferably 0.1 to 8.0 mol %, in terms of molar ratio of the acid contained in the acidic solution, relative to the total number of moles of the compound containing the element X and the compound containing the element Z.

The amount of the acidic solution to be used in the case where the catalyst contains the other element such as the zinc element is preferably 0.01 to 10.0 mol %, and more preferably 0.1 to 8.0 mol %, relative to the total number of moles of the compound containing the element X, the compound containing the element Z, and the compound containing the other element.

Basic Aqueous Solution

The basic solution has a function of accelerating the generation of solids through the hydrolysis described below. In general, one of the above-mentioned acidic aqueous solution and basic aqueous solution is used.

Examples of the basic solution include, but are not particularly limited to, an aqueous solution in which an inorganic base such as sodium hydroxide, calcium carbonate, or ammonia is dissolved.

The amount of the basic solution to be used in the case where the catalyst does not contain the other element such as the zinc element is preferably 0.01 to 10.0 mol %, and more preferably 0.1 to 8.0 mol %, relative to the total number of moles of the compound containing the element X and the compound containing the element Z.

The amount of the basic solution to be used in the case where the catalyst contains the other element such as the zinc element is preferably 0.01 to 10.0 mol %, and more preferably 0.1 to 8.0 mol %, relative to the total number of moles of the compound containing the element X, the compound containing the element Z, and the compound containing the other element.

The method for preparing the mixture is not particularly limited. For example, the mixture may be prepared by a method in which the compound containing the element X, the compound containing the element Z, and the surfactant are mixed, followed by addition of water and the organic solvent, or a method in which the compound containing the element X and the surfactant are mixed, followed by addition of water and the organic solvent, and finally the compound containing the element Z is added to the resulting mixture. When the compound containing the other element (preferably a compound containing zinc) is used, water and the organic solvent may be added after mixing the compound containing the element X, the compound containing element Z, the compound containing zinc, and the surfactant, or may be added after mixing the compound containing the element X, the compound containing zinc, and the surfactant, which is then followed by finally adding the compound containing the element Z.

The mixture described above is generally obtained in the form of a suspension. More specifically, the compound containing the element X and the compound containing the element Z in the mixture are hydrolyzed and condensed by the presence of water to form solids, thereby forming a suspension.

Preferably, the mixture described above is stirred and matured to form the solids. In the context of the present specification, the term maturation refers to an act of allowing the mixture to stand.

In this case, the mixing temperature for the mixture is preferably 20 to 150° C. and more preferably 30 to 60° C.

The mixing time for the mixture is preferably from 1 hour to 10 days and more preferably from 10 hours to 5 days.

The maturation temperature for the mixture is preferably 50 to 200° C. and more preferably 80 to 150° C.

The maturation time for the mixture is preferably 1 hour to 10 days and more preferably 10 hours to 5 days.

(Preparation of Solid Colloid)

The solid colloid can be obtained by distilling off at least a part of the solvent (water, an organic solvent, etc.) from the mixture (usually a suspension) obtained as described above. Higher homogeneity of the catalyst is achievable by producing the catalyst through a process forming the solid colloid as compared to the case of producing the catalyst by direct calcination of the suspension. In the context of the present specification, the term "solid colloid" refers to one with a solvent content of 5% or less, based on the total volume of the solid colloid.

The temperature for obtaining the solid colloid, i.e., the temperature for distilling off at least a part of the solvent, is preferably 20 to 200° C., and more preferably 50 to 150° C.

The time for obtaining the solid colloid, i.e., the time for distilling off at least a part of the solvent, is preferably from 1 hour to 10 days and more preferably from 10 hours to 5 days.

[Calcination Step]

The calcination step is a step of calcining the solid colloid obtained in the solid colloid preparation step described above. By calcination of the solid colloid, the surfactant is removed from the composite oxide precursor which has template micelles formed by the surfactant, thereby enabling the production of a catalyst having mesopores.

The calcination temperature is preferably 200 to 800° C., and more preferably 400 to 600° C. The calcination temperature of 200° C. or higher is preferable in that no or almost no impurities derived from the surfactant remain in the catalyst. On the other hand, the calcination temperature of not higher than 800° C. is preferable in that the stability of the crystal structure of the pore walls forming the mesopores of the catalyst can be improved.

The calcination time is preferably 10 minutes to 2 days, and more preferably 1 to 10 hours. The calcination time of 10 minutes or more is preferable in that no or almost no impurities derived from the surfactant remain in the catalyst. On the other hand, the calcination time of 2 day or less is preferable in that the stability of the crystal structure of the pore walls forming the mesopores of the catalyst can be improved.

(Apparatus for Producing Diene Compound)

The apparatus for producing a diene compound includes a reaction tube filled with the catalyst described above. The apparatus is used for producing a diene compound from a raw material gas containing a raw material.

Hereinbelow, a butadiene production apparatus, which is one type of the apparatus for producing a diene compound, is described with reference to FIG. 1.

The butadiene production apparatus 10 of the present embodiment (hereinafter, simply referred to as "production apparatus 10") includes a reaction tube 1, a supply pipe 3, an outlet pipe 4, a temperature controller 5, and a pressure controller 6.

The reaction tube 1 has a reaction bed 2 inside. The reaction bed 2 is packed with the synthesis catalyst of the present invention. The supply pipe 3 is connected to the reaction tube 1. The outlet pipe 4 is connected to the reaction tube 1. The temperature controller 5 is connected to the reaction tube 1. The outlet pipe 4 is equipped with the pressure controller 6.

The reaction bed 2 may have only the catalyst of the present invention, or may have another catalyst as well as the catalyst of the present invention. Further, the reaction bed 2 may also contain a diluent. The diluent prevents the catalyst from generating excessive heat.

In this context, the reaction for synthesizing butadiene from the raw material is an endothermic reaction. For this reason, the reaction bed 2 usually does not require a diluent.

The diluent may be, for example, quartz sand, alumina balls, aluminum balls, aluminum shots, and the like.

When a diluent is charged into the reaction bed 2, the mass ratio, diluent/synthesis catalyst, is determined in consideration of the type, specific gravity and the like of the diluent and the synthesis catalyst, and is, for example, preferably 0.5 to 5.

The reaction bed may be any of a fixed bed, a moving bed, a fluidized bed, and the like.

The reaction tube 1 is preferably made of a material that is inert to the raw material gas and the synthesized product. The reaction tube 1 preferably has a shape that enables the reaction tube 1 to withstand heating at about 100 to 500° C. or pressurization at about 10 MPa. The reaction tube 1 may be, for example, a substantially cylindrical member made of stainless steel.

The supply pipe 3 is a supply means that supplies the raw material gas into the reaction pipe 1. The supply pipe 3 is, for example, a pipe made of stainless steel.

The outlet pipe 4 is an outlet means that releases a gas containing a product synthesized in the reaction bed 2. The outlet pipe 4 is, for example, a pipe made of stainless steel or the like.

With respect to the temperature controller 5, there is no particular limitation as long as it can control the temperature of the reaction bed 2 in the reaction tube 1 to a desired value. For example, the temperature controller 5 may be an electric furnace or the like.

With respect to the pressure controller 6, there is no particular limitation as long as it can control the internal pressure of the reaction tube 1 to a desired value. For example, the pressure controller 6 may be a known pressure valve or the like.

The production apparatus 10 may be equipped with a known device such as a gas flow rate controller (e.g., mass flow controller) or the like which adjusts a flow rate of the gas.

<Method for Producing Diene Compound>

The present invention in one aspect thereof provides a method for producing a diene compound. The method for producing a diene compound includes contacting a raw material gas containing an alcohol with the catalyst of the present invention to thereby produce a diene compound.

[Catalyst]

The catalyst to be used is as described above and therefore detailed descriptions are omitted here.

The amount of the catalyst to be used is preferably 0.1 to 10 g/g·h, and more preferably 1 to 5 g/g·h, based on the amount of the raw material gas. The catalyst amount of not less than 0.1 g/g·h is favorable in that the reaction conversion can be improved. On the other hand, the catalyst amount of not more than 10 g/g·h is favorable in that generation of by-products can be suppressed.

[Raw Material Gas]

The raw material gas contains an alcohol. In addition, the raw material gas may further include an aldehyde, an inert gas, and the like.

(Alcohol)

Examples of the alcohol include, but are not particularly limited to, alcohols having 1 to 6 carbon atoms. Specific examples of the alcohol include methanol, ethanol, propanol, butanol, pentanol, hexanol and the like.

In principle, the diene compound to be obtained depends on the type of alcohol used. For example, when ethanol is used, butadiene is obtained. When propanol is used, hexadiene is obtained. When butanol is used, octadiene is obtained.

The alcohol used may be of a single type or a mixture of two or more types, but is preferably of a single type from the viewpoint of suppressing side reactions.

The concentration of the alcohol in the raw material gas is preferably 10% by volume or more, more preferably 15% by volume or more, even more preferably 20% by volume or more, even more preferably 30% by volume or more, particularly preferably 50% by volume or more, and most preferably from 75% by volume or more, with respect to 100% by volume of the raw material gas. When two or more different alcohols are used in combination, the sum of the amounts thereof is preferably within in the above range. The use of the catalyst according to the present invention enables the reaction to proceed efficiently even when the alcohol concentration in the raw material gas is high.

(Aldehyde)

Aldehydes are usually oxides of alcohols. Specific examples thereof include formaldehyde, acetaldehyde, propionaldehyde, butyraldehyde, valeraldehyde, and the like.

When the raw material gas contains an aldehyde, the aldehyde is generally one corresponding to the alcohol. Specifically, when methanol is used as the alcohol, the aldehyde is formaldehyde. Likewise, the aldehyde is acetaldehyde when using ethanol as the alcohol, the aldehyde is propionaldehyde when using propanol as the alcohol, the aldehyde is butyraldehyde when using butanol as the alcohol, and the aldehyde is valeraldehyde when using pentanol as the alcohol. However, the aldehyde may include an aldehyde other than the aldehyde corresponding to the alcohol.

The concentration of the aldehyde in the raw material gas is preferably 1% by volume or more, more preferably 5% by volume or more, even more preferably 10% by volume or more, particularly preferably 50% by volume or more, and most preferably from 75 to 99% by volume, with respect to 100% by volume of the raw material gas. When two or more different alcohols are used in combination, the sum of the amounts thereof is preferably within in the above range.

The total concentration of the alcohol and the aldehyde in the raw material gas is preferably 15% by volume or more, more preferably 20% by volume or more, and even more preferably 20 to 40% by volume, with respect to 100% by volume of the raw material gas.

(Inert Gas)

Examples of the inert gas include, but are not particularly limited to, nitrogen gas and argon gas. One of these inert gases may be used alone or two or more of these may be used in combination.

The concentration of the inert gas is preferably 90% by volume or less, more preferably 30 to 90% by volume, even more preferably 50 to 90% by volume, and particularly preferably 60 to 80% by volume, with respect to 100% by volume of the raw material gas.

[Contacting]

With respect to the method for bringing the raw material gas into contact with the catalyst, there is no particular limitation. A preferred example thereof is a method in which the raw material gas is passed through the reaction bed in the reaction tube so as to allow the synthesis catalyst in the reaction bed to contact the raw material gas.

The temperature (reaction temperature) at which the catalyst is brought into contact with the raw material gas is preferably from 100 to 600° C., more preferably from 200 to 500° C., and even more preferably from 250 to 450° C. The reaction temperature of not lower than 100° C. is favorable in that the reaction rate is sufficiently increased, and the diene compound can be produced more efficiently. On the other hand, the reaction temperature of not higher than 600° C. is favorable in that deterioration of the catalyst can be prevented or suppressed.

The pressure (reaction pressure) at which the raw material gas is brought into contact with the catalyst is preferably 0.1 to 10 MPa, and more preferably 0.1 to 3 MPa. The reaction pressure of not less than 0.1 MPa is favorable in that the reaction rate is increased, and the diene compound can be produced more efficiently. On the other hand, the reaction pressure of not more than 10 MPa is favorable in that deterioration of the catalyst can be prevented or suppressed.

The space velocity (SV) of the raw material gas in the reaction bed is usually adjusted appropriately in consideration of the reaction pressure and the reaction temperature, but is preferably 0.1 to 10000 $h^{-1}$ in terms of the value under the standard condition.

For example, when butadiene is produced using the production apparatus 10, the temperature controller 5 and the pressure controller 6 adjust the internal temperature and pressure of the reaction tube 1 to the respective predetermined values. The raw material gas 20 is supplied from the supply pipe 3 into the reaction tube 1. In the reaction tube 1, the raw material comes into contact with the synthesis catalyst and reacts to generate butadiene. The product gas 22 containing butadiene is released from the outlet pipe 4. The product gas 22 may also contain compounds such as acetaldehyde, propylene, and ethylene.

With respect to the product gas containing the diene compound (product gas 22 in FIG. 1), the product gas is subjected to purification such as gas-liquid separation or distillation purification as necessary to remove unreacted raw material and by-products.

The present invention also enables the production of a diene compound from bioethanol to thereby reduce the environmental burden.

EXAMPLES

Hereinbelow, the present invention will be described with reference to Examples which, however, should not be construed as limiting the present invention.

Example 1

2 g of P123 ($[(HO(CH_2CH_2O)_{20}(CH_2CH(CH_3)O)_{70}(CH_2CH_2O)_{20})H]$, manufactured by BASF Co., Ltd.) as a surfactant was charged into a beaker, followed by addition of 65 mL of water, and the resulting was stirred to dissolve the surfactant. To the resulting aqueous solution having the surfactant dissolved therein, hafnium chloride ($HfCl_4$) and zinc nitrate hexahydrate ($Zn(NO_3)_2.6H_2O$) were added, followed by stirring to dissolve the metal chloride. Then, tetraethoxysilane was added to the resulting, thereby preparing a raw material solution. The obtained raw material solution was stirred at 40° C. for 20 hours. Thereafter, the solution was heated to 100° C. and allowed to stand for 20 hours.

Next, 35 mL of 2N hydrochloric acid was added to the raw material solution and the resulting was stirred at 40° C. for 20 hours to obtain a suspension.

The obtained suspension was allowed to mature at 100° C. for 20 hours, filtered, washed with ethanol and water. Then, the resulting powder was transferred to a petri dish and dried in an oven maintained at a temperature of 110° C. to obtain a solid colloid.

The obtained solid colloid was calcined in an electric furnace at 550° C. for 5 hours under an air atmosphere, thereby obtaining a catalyst which was a composite oxide containing Hf, Si and Zn.

The molar amounts (mol %) of Hf and Zn in the obtained catalyst were measured by the following method. That is, a certain amount of the obtained catalyst was weighed, decomposed by alkali melting, dissolved in an acid, and the volume of the resulting solution was fixed to obtain a test solution. The molar amounts (mol %) of Hf and Zn in the test solution were measured by an ICP emission spectrometer. As a result, the molar amount of Hf was found to be 1.56 mol %, and the molar amount of Zn was found to be 2.02 mol %. Further, the molar amount of Si (mol %) is a value obtained by subtracting the Hf molar amount and the Zn molar amount from 100. Therefore, the molar amount of Si in the catalyst was 96.42 mol %.

Further, the average pore diameter of the catalyst was measured as follows. That is, a certain amount of the catalyst was weighed, and the average pore diameter of the catalyst was measured by a gas adsorption method. As a result, the average pore diameter of the catalyst was found to be 2.5 nm.

The results are shown in Table 1.

Examples 2 to 8

A catalyst was produced in the same manner as in Example 1, except that the amounts of tetraethoxysilane, hafnium (IV) chloride, and zinc nitrate hexahydrate were adjusted so that the molar amounts of X and Zn in the catalyst were as shown in Table 1.

The molar amounts of the elements X and Zn, and the average pore diameter of the catalyst were measured in the same manner as in Example 1.

The results are shown in Table 1.

Examples 9 to 15

A catalyst was produced in the same manner as in Example 1, except that a salt of the element X other than hafnium chloride (IV) was used.

The molar amounts of the elements X and Zn, and the average pore diameter of the catalyst were measured in the same manner as in Example 1.

The results are shown in Table 1.

Comparative Example 1

A catalyst was prepared in the same manner as in Example 1, except that hafnium chloride ($HfCl_4$) and zinc nitrate hexahydrate ($Zn(NO_3)_2 \cdot 6H_2O$) were not used.

Further, the average pore diameter of the catalyst was measured in the same manner as in Example 1.

The results are shown in Table 1.

Specifically, 3.4 g of the catalyst was filled into a cylindrical reaction tube made of stainless steel and having a diameter of ½ inch (1.27 cm) and a length of 15.7 inch (40 cm) to form a reaction bed. Next, the reaction temperature (reaction bed temperature) was set to 350° C. or 300° C., and the reaction pressure (reaction bed pressure) was set to 0.1 MPa. A raw material gas was supplied to the reaction tube at an SV of 1200 L/hr/catalyst amount (L-catalyst) to obtain a product gas. The raw material gas was a mixed gas of 15% by volume (in terms of gas volume) of ethanol, 15% by volume (in terms of gas volume) of acetaldehyde, and 70% by volume (in terms of gas volume) of nitrogen.

The recovered product gas was analyzed by gas chromatography to determine the BD selectivity, ethylene selectivity, conversion, and BD yield ([conversion]×[BD selectivity]). The "BD selectivity" means a percentage of the number of moles of the raw material converted to butadiene out of the number of moles of the raw material consumed in the reaction using the catalyst. In this evaluation, since both ethanol and acetaldehyde are used as the raw materials, the total number of moles of these compounds is the number of moles of the raw materials. The "conversion (raw material conversion)" means a percentage of the number of moles of the raw materials consumed out of the number of moles of the raw materials contained in the raw material gas.

The results are shown in Table 1.

TABLE 1

| | Element A | | Zinc | | Pore diameter (nm) | Reaction temperature | Selectivity (%) | | Conversion (%) | BD yield (%) |
|---|---|---|---|---|---|---|---|---|---|---|
| | Type | Amount (mol %) | Type | Amount (mol %) | | | BD | Ethylene | | |
| Ex. 1 | Hf | 1.56 | Zn | 2.02 | 2.5 | 350 | 84.7 | 6.3 | 82.3 | 70 |
| Ex. 2 | Hf | 2.5 | Zn | 2.29 | 3.5 | 350 | 74.7 | 13.6 | 99.9 | 75 |
| Ex. 3 | Hf | 3.43 | Zn | 2.43 | 10.4 | 350 | 70.2 | 16.7 | 99.9 | 70 |
| Ex. 4 | Hf | 2.5 | Zn | 1.1 | 11.6 | 350 | 68.3 | 15.3 | 99.9 | 68 |
| Ex. 5 | Hf | 2.71 | Zn | 0.14 | 12.4 | 350 | 65.6 | 18.2 | 99.9 | 66 |
| Ex. 6 | Hf | 2.57 | Zn | 0 | 12.5 | 350 | 60.2 | 32.8 | 65.4 | 39 |
| Ex. 7 | Hf | 7.47 | Zn | 0 | 12.7 | 350 | 15.9 | 72 | 45.9 | 7.3 |
| Ex. 8 | Hf | 2.5 | Zn | 2.29 | 3.5 | 300 | 36.7 | 13.6 | 99.9 | 37 |
| Ex. 9 | La | 2.5 | Zn | 2.29 | 6.5 | 350 | 43.2 | 37.5 | 70.5 | 30 |
| Ex. 10 | Ti | 2.5 | Zn | 2.29 | 7.2 | 350 | 38.4 | 61.9 | 65 | 25 |
| Ex. 11 | Zr | 2.5 | Zn | 2.29 | 6.6 | 350 | 70.6 | 12.5 | 90.8 | 64 |
| Ex. 12 | V | 2.5 | Zn | 2.29 | 5.8 | 350 | 42.2 | 312 | 1.7 | 0.7 |
| Ex. 13 | Nb | 2.5 | Zn | 2.29 | 6.6 | 350 | 64.4 | 27.1 | 85.1 | 55 |
| Ex. 14 | Ta | 2.5 | Zn | 2.29 | 7.7 | 350 | 45 | 27.1 | 85.1 | 38 |
| Ex. 15 | W | 2.5 | Zn | 2.29 | 7.1 | 350 | 8.3 | 83.6 | 46.4 | 3.8 |
| Comp. Ex. 1 | Hf | 0 | Zn | 0 | 12.5 | 350 | 0 | 0 | 0 | 0 |
| Comp. Ex. 2 | Hf | 15.7 | Zn | 42.9 | —* | 350 | 0 | 2.5 | 10 | 0 |

Comparative Example 2

Silica, hafnium oxide and zinc oxide were mixed and ground in a mortar using a pestle. The resulting was transferred to a crucible and calcined at 700° C. for 5 hours to produce a catalyst which was a composite oxide containing Hf, Zn and Si.

The molar amounts of the elements X and Zn, and the average pore diameter of the catalyst were measured in the same manner as in Example 1.

The results are shown in Table 1.

(Evaluation Method)

Using the catalysts produced in Examples 1 to 15 and Comparative Examples 1 and 2, a reaction was performed to produce 1,3-butadien from ethanol to determine the 1,3-butadiene (BD) selectivity, conversion, and yield of 1,3-butadiene (BD). Further, the selectivity for ethylene was measured as well.

The results in Table 1 show that the catalysts of Examples 1 to 15 can be suitably used to obtain 1,3-butadiene even when large amounts of ethanol and acetaldehyde are contained in the raw material gas.

DESCRIPTION OF THE REFERENCE SIGNS

1 Reaction tube
2 Reaction bed
3 Supply pipe
4 Outlet pie
5 Temperature controller
6 Pressure controller
10 Butadiene production apparatus

The invention claimed is:
1. A catalyst which is a composite oxide comprising at least one element X selected from the group consisting of elements belonging to Groups 3 to 6 of the periodic table, and at least one element Z selected from the group consisting of elements belonging to Group 14 of the periodic table,
wherein the catalyst has mesopores, and
wherein a peak ascribed to a periodic structure of the mesopores is observed at a low angle of 2θ=1 to 6° in an X-ray diffraction pattern.

2. The catalyst according to claim 1, which satisfies formula 1:

$$X_{a1}Si_{b1}O_{\delta1} \quad \text{Formula 1}$$

wherein:
- a1 is a molar ratio of the element X, and is 0.1 to 20 mol % with the proviso that a sum of a1 and b1 is 100 mol %;
- b1 is a molar ratio of Si, and is 80 to 99.9 mol % with the proviso that a sum of a1 and b1 is 100 mol %; and
- δ1 represents a number required to satisfy a charge neutral condition.

3. The catalyst according to claim 1, which further comprises a zinc element (Zn).

4. The catalyst according to claim 3, which satisfies formula 2:

$$X_{a2}Si_{b2}Zn_{c2}O_{\delta2} \quad \text{Formula 2}$$

wherein:
- a2 is a molar ratio of the element X, and is 0.1 to 20 mol % with the proviso that a sum of a2, b2 and c2 is 100 mol %;
- b2 is a molar ratio of Si, and is 60 to 99.8 mol % with the proviso that a sum of a2, b2 and c2 is 100 mol %;
- c2 is a molar ratio of Zn, and is 0.1 to 20 mol % with the proviso that a sum of a2, b2 and c2 is 100 mol %; and
- δ2 represents a number required to satisfy a charge neutral condition.

5. The catalyst according to claim 1, which is a catalyst for synthesizing a diene compound from a raw material gas containing an alcohol.

6. The catalyst according to claim 5, wherein the raw material gas comprises ethanol, acetaldehyde or a mixture of ethanol and acetaldehyde.

7. The catalyst according to claim 1, wherein the element X is a hafnium element (Hf).

8. The catalyst according to claim 7, which further comprises a zinc element (Zn).

9. The catalyst according to claim 8, which does not comprise a tantalum element (Ta).

10. The catalyst according to claim 8, which does not comprise a niobium element (Nb).

11. The catalyst according to claim 8, which does not comprise a tantalum element (Ta) and a niobium element (Nb).

12. The catalyst according to claim 7, which does not comprise a tantalum element (Ta).

13. The catalyst according to claim 7, which does not comprise a niobium element (Nb).

14. The catalyst according to claim 7, which does not comprise a tantalum element (Ta) and a niobium element (Nb).

* * * * *